United States Patent [19]

Ledouble et al.

[11] 4,423,220
[45] Dec. 27, 1983

[54] PROCESS FOR THE PRODUCTION OF O,O-DIALKYLPHOSPHORODITHIOATES

[75] Inventors: Jean-Pierre Ledouble, St. Louis, France; Markus Tschopp, Liestal, Switzerland

[73] Assignee: Ciba-Geigy Corporation, Ardsley, N.Y.

[21] Appl. No.: 97,592

[22] Filed: Nov. 26, 1979

Related U.S. Application Data

[63] Continuation of Ser. No. 636,780, Dec. 1, 1975, abandoned.

[51] Int. Cl.³ .................................................. C07F 9/65
[52] U.S. Cl. ..................................................... 546/22
[58] Field of Search ........................................... 546/22

[56] References Cited

U.S. PATENT DOCUMENTS

| | | | |
|---|---|---|---|
| 3,130,217 | 4/1964 | Dickhaeuser et al. | 260/944 |
| 3,232,830 | 2/1966 | Schrader et al. | 424/216 |
| 3,833,600 | 9/1974 | Toepfl | 546/22 |

OTHER PUBLICATIONS

Smith, P., *The Chemistry of Open-Chain Organic Nitrogen Compounds,* vol. 1, W. A. Benjamin, New York, 1965, p. 152.
Ronwin, *J. Org. Chem.,* 18, 127–132, (1953).
*Chemical Abstracts,* 61: 6987b, (1964) [Parrot, J., et al.] *Compt. Rend.* 258(24), 5898–5899, (1964).

*Primary Examiner*—Richard A. Schwartz
*Attorney, Agent, or Firm*—Karl F. Jorda; Bruce M. Collins

[57] ABSTRACT

A new process for the production of O,O-dialkylphosphorodithioates of the formula

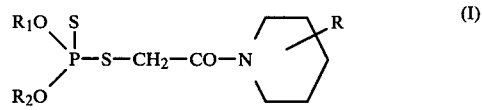

(I)

wherein R represents methyl or ethyl, and $R_1$ and $R_2$ are identical or different, and each represent an alkyl, alkenyl or alkoxyalkyl group having in each case at most 5 carbon atoms is disclosed. The process comprises reacting an essentially equimolar mixture of a piperidine of the formula

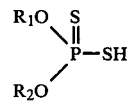

(II)

and a free O,O-dialkyldithiophosphoric acid of the formula

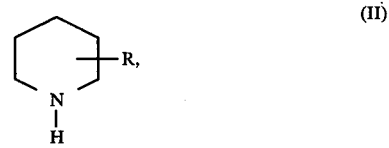

or a sodium, potassium or ammonium salt thereof, in the presence of an acid binding agent, with chloroacetylchloride.

9 Claims, No Drawings

PROCESS FOR THE PRODUCTION OF O,O-DIALKYLPHOSPHORODITHIOATES

This is a continuation of application Ser. No. 636,780 filed on Dec. 1, 1975, now abandoned.

The present invention relates to a process for the production of O,O-dialkylphosphorodithioates of the formula

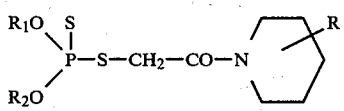

wherein R represents mehtyl or ethyl, and $R_1$ and $R_2$ are identical or different, and each represent an alkyl, alkenyl or alkoxyalkyl group having in each case at most 5 carbon atoms.

The O,O-dialkylphosphorodithioates of the formula I are selective herbicides which are suitable, in particular, for the control of weeds in rice crops. These compounds and their use are described in the U.S. Pat. No. 3,833,600. One compound of the formula I, namely O,O-di-n-propyl-s-(2-(2'-methyl-1-piperidinyl)-2-oxoethyl)-phosphorodithioate, is also described in the Pesticide Manual, 4th Edition, British Crop Protection Council, November, 1974.

According to U.S. Pat. No. 3,833,600, the compounds of the formula I are produced by reacting in an inert solvent a salt, for example the sodium or potassium sat of a O,O-dialkyldithiophosphate of the formula

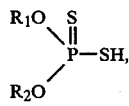

wherein $R_1$ and $R_2$ have the meaning defined above, with a chloroacetylpiperidine of the formula

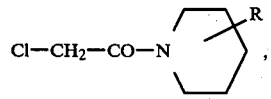

wherein R has the meaning given above. The chloroacetylpiperidines required as starting material are for their part obtained by reaction of chloroacetyl chloride with a corresponding piperidine substituted by the radical R according to the above definition.

According to an alternative likewise mentioned in the U.S. Pat. No. 3,833,600, the O,O-dialkylphosphorodithioates of the formula I can be produced also by reacting an ester of a O,O-dialkyldithiophosphorylacetic acid, e.g. the phenyl ester, benzyl ester or ethylene glycol ester, with the piperdine substituted by the radical R. In this process, the ester of a O,O-dialkyldithiophosphorylacetic acid, used as starting material, has to be produced in a preliminary step by reaction of the sodium or potassium salt of a O,O-dialkyldithiophosphoric acid with a corresponding chloroacetic acid ester. A disadvantage of this process is that two separate reaction steps have to be performed before the desired final products of the formula I are obtained. The object of the present invention is therefore to simplify the known production processes and, simultaneously, to increase the attainable yield of the desired final product of the formula I.

The process according to the invention for the production of O,O-dialkylphosphorodithioates of the formula I comprises reacting an essentially equimolar mixture of a piperidine of the formula II

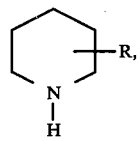

wherein R has the meaning given under formula I, and a free O,O-dialkyldithiophosphoric acid of the formula III

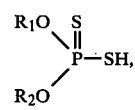

wherein $R_1$ and $R_2$ have the meaning defined above, or a sodium, potassium or ammonium salt thereof, in the presence of an acid-binding agent, with chloroacetyl chloride.

The reaction can be performed in the absence of a solvent. Preferably, however, the reaction is carried out in a two-phase system consisting of water and an organic solvent immiscible with water. Suitable solvents are aliphatic and aromatic hydrocarbons such as hexane, cyclohexane, benzene and, in particular, toluene, as well as halogenated hydrocarbons such as chlorobenzene, dichloroethane, trichloroethylene, methylene chloride, and carbon tetrachloride.

The process of the invention can be performed in the temperature range of between 0° and 20° C., preferably it is performed at between 5° and 15° C. The reaction occurs practically immediately after addition of the halogenoacetyl halide. The duration of the reaction is therefore governed virtually by the extent to which the evolved heat of reaction can be conducted away to maintain the aforementioned temperatures. The reaction can normally be performed within 10 minutes to 4 hours.

There are used for the reaction essentially equimolar amounts of the reactants, with slightly more or slightly less than the equivalent amount of the one or of the other reactant being possible.

Suitable acid-binding agents are alkali metal hydroxides or alkaline-earth metal hydroxides. The acid-binding agent preferably used is sodium hydroxide or potassium hydroxide. The amount of acid-binding agent is preferably 2 moles per mole of piperidine of the formula II to be reacted. If the O,O-dialkyldithiophosphoric acid of the formula III is used in the form of the sodium or potassium salt, then 1 mole of acid-binding agent per mole of reacted piperidine of the formula II is sufficient.

A preferred embodiment of the process of the invention comprises adding one equivalent of chloroacetyl chloride at a temperature of between 5° and 15° C., with vigorous stirring, to a two-phase system consisting of a solution of a piperidine of the formula II in toluene and an aqueous solution of one equivalent of an alkali salt of a O,O-dialkyldithiophosphoric acid of the formula III and one equivalent of sodium or potassium hydroxide.

The process of the invention has the advantage not only that the production of O,O-dialkylphosphorodithioates of the formula I is simplified but also that the desired final products are obtained in better yield than they are in the known two-stage process. This has to be regarded as surprising since with each of its two reactive chlorine atoms chloroacetyl chloride can react essentially either with the piperidine of the formula II or with the O,O-dialkyldithiophosphoric acid of the formula III. Surprisingly, however, the reaction occurs uniformly and the O,O-dialkylphosphorodithioates of the formula I are formed in yields in excess of 90% of theory. A further advantage of the process of the invention is that the ecological difficulties are reduced compared with those arising with the conventional two-stage process.

The process of the invention is further illustrated by the following Examples.

EXAMPLE 1

Into a two-phase system consisting of 50 ml of toluene and 30 ml of water there are placed 9.9 g (0.1 mole) of 2-methylpiperidine, 26.0 g (0.103 mole) of the potassium salt of O,O-di-n-propyldithiophosphoric acid and 5.0 g (0.125 mole) of sodium hydroxide. To this mixture there is then added dropwise at 5° to 15° C., with stirring, 11.8 g (0.104 mole) of chloroacetyl chloride. After completion of the addition, the reaction mixture is heated, with further stirring, to room temperature. The organic phase is afterwards separated and washed with water until neutral, and the solvent is distilled off at 80° C. and 20 Torr. There is obtained as residue 34.9 g of a yellow oil consisting to the extent of 94% of O,O-di-n-propyl-s-[2-(2'-methyl-1-piperidinyl)-2-oxoethyl]-dithiophosphate, which corresponds to a net yield of 93% of theory relative to 2-methylpiperidine.

EXAMPLE 2

110 g (0.515 mole) of O,O-di-n-propyldithiophosphoric acid and 50 g (0.503 mole) of 2-methylpyridine are introduced, with stirring, into a two-phase mixture, cooled to 15° C., consisting of 250 g of toluene and 150 g of 30% aqueous sodium hydroxide solution (1.12 moles of NaOH). To the mixture obtained there is subsequently added dropwise, at 8° to 12° C., 60 g (0.506 mole) of chloroacetyl chloride. After completion of the addition, the reaction mixture is briefly heated to 25° C. and 60 ml of water is added. The aqueous phase is separated from the mixture neutralised by addition of about 5 g of 80% sulphuric acid, and the organic phase is extracted with 120 ml of water, whereupon the aqueous phase is neutralised afresh by the addition of about 1 ml of 80% sulphuric acid. The aqueous phase is afterwards separated and the organic phase is freed from the solvent in vacuo. There is obtained 175 g of a yellow oil consisting to the extent of 93% of O,O-di-n-propyl-S-[2-(2'-methyl-1-piperidinyl)-2-oxoethyl]-dithiophosphate, an amount corresponding to a yield of 93% of theory relative to the amount of 2-methylpyridine used.

We claim:

1. In the production of an O,O-disubstituted phosphorodithioate of the formula:

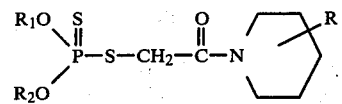

wherein
R is methyl or ethyl and
each of $R_1$ and $R_2$, independently of the other, is alkyl, alkenyl or alkoxyalkyl having a maximum total of 5 carbon atoms, the improvement permitting said production directly which comprises simultaneously bringing into contact under reactive conditions essentially equimolar amounts of the reactants (a) chloroacetyl chloride, (b) a methyl- or ethylpiperidine of the formula:

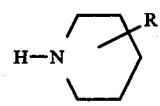

wherein R is as herein defined, and (c) a source of the anion of an O,O-disubstituted dithiophosphoric acid of the formula:

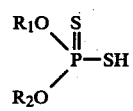

wherein $R_1$ and $R_2$ are as herein defined, in the presence of at least an essentially equimolar amount of an acid binding agent.

2. The process according to claim 1 wherein said reactants are brought into contact in a two-phase system consisting of water and an organic solvent immiscible with water.

3. The process according to claim 2 wherein said organic solvent is an aliphatic or aromatic hydrocarbon or an aliphatic or aromatic halogenated hydrocarbon.

4. The process according to claim 3 wherein said organic solvent is toluene.

5. The process according to claim 1 wherein the reaction is conducted at temperatures between 0° C. and 20° C.

6. The process according to claim 5 wherein the reaction is conducted at temperatures of from 5° C. to 15° C.

7. The process according to claim 1 wherein the acid binding agent is an alkali metal hydroxide or alkaline earth metal hydroxide.

8. The process according to claim 7 wherein the acid binding agent is sodium hydroxide or potassium hydroxide.

9. The process according to claim 1 wherein essential equimolar amounts of chloroacetyl chloride, 2-methylpiperidine and a source of the anion of O,O-di-n-propyldithiophosphoric acid are simultaneously brought into contact in an agitated two phase system of water and toluene at temperatures of between 5° C. and 15° C. in the presence of an essentially equimolar amount of an alkali metal hydroxide.

* * * * *